United States Patent
Völkl et al.

(10) Patent No.: US 11,040,909 B2
(45) Date of Patent: Jun. 22, 2021

(54) METHOD TO INCREASE THE STRENGTH OF A FORM BODY OF A LITHIUM SILICATE GLASS CERAMIC

(71) Applicant: DENTSPLY SIRONA Inc., York, PA (US)

(72) Inventors: Lothar Völkl, Goldbach (DE); Stefan Fecher, Johannesberg (DE)

(73) Assignee: DENTSPLY SIRONA Inc., York, PA (US)

( * ) Notice: Subject to any disclaimer, the term of this patent is extended or adjusted under 35 U.S.C. 154(b) by 322 days.

(21) Appl. No.: 15/160,529

(22) Filed: May 20, 2016

(65) Prior Publication Data
US 2016/0340238 A1 Nov. 24, 2016

(51) Int. Cl.
| | | |
|---|---|---|
| *C03B 25/00* | (2006.01) |
| *C03C 17/22* | (2006.01) |
| *C03C 21/00* | (2006.01) |
| *C03C 4/00* | (2006.01) |
| *C03C 3/097* | (2006.01) |
| *A61K 6/20* | (2020.01) |

(Continued)

(52) U.S. Cl.
CPC .............. *C03C 21/002* (2013.01); *A61K 6/20* (2020.01); *A61K 6/804* (2020.01); *A61K 6/818* (2020.01); *A61K 6/822* (2020.01); *A61K 6/833* (2020.01); *A61K 6/853* (2020.01); *C03B 25/00* (2013.01); *C03C 3/097* (2013.01); *C03C 4/0021* (2013.01); *C03C 10/0027* (2013.01); *C03C 17/22* (2013.01); *C03C 2204/00* (2013.01)

(58) Field of Classification Search
CPC ................................ C03B 32/00; C03C 21/00
See application file for complete search history.

(56) References Cited

U.S. PATENT DOCUMENTS 3,791,809 A 2/1974 Lau
3,912,480 A * 10/1975 Boguslavsky .......... C03B 25/02
264/70

(Continued)

FOREIGN PATENT DOCUMENTS

| BE | 618738 A | 12/1962 |
| DE | 3015529 A1 | 11/1980 |
| FR | 2454796 A1 | 11/1980 |

OTHER PUBLICATIONS

I.L. Denry et al; Enhanced Chemical Strengthening of Feldspathic Dental Porcelain; J Dent Res; Oct. 1993; pp. 1429-1433.

(Continued)

*Primary Examiner* — Cynthia Szewczyk
(74) *Attorney, Agent, or Firm* — DENTSPLY SIRONA Inc.

(57) ABSTRACT

The invention relates to a method to increase the strength of a form body of lithium silicate glass ceramic, which after it has a desired end geometry and after the application of a material which influences its surface to form a coating, is subject to a heat treatment. To create a surface compressive stress through the replacement of lithium ions by alkali ions of greater diameter at least that region not covered by the application layer is covered by a melt or paste consisting of or containing a salt of an alkali metal with ions of greater diameter and the form body is in contact with the melt or paste for a period of time t at a temperature T and the melt or paste is subsequently removed from the form body.

21 Claims, 1 Drawing Sheet

(51) Int. Cl.
*A61K 6/804* (2020.01)
*A61K 6/818* (2020.01)
*A61K 6/822* (2020.01)
*A61K 6/833* (2020.01)
*A61K 6/853* (2020.01)
*C03C 10/00* (2006.01)

(56) References Cited

U.S. PATENT DOCUMENTS

| | | | |
|---|---|---|---|
| 4,784,606 A | 11/1988 | Jones | |
| 4,874,414 A * | 10/1989 | Kaite | C03C 21/001 65/30.13 |
| 5,705,273 A * | 1/1998 | Denry | C03C 21/008 427/2.27 |
| 6,420,288 B2 | 7/2002 | Schweiger | |
| 8,956,987 B2 | 2/2015 | Durschang | |
| 9,206,077 B2 | 12/2015 | Durschang | |
| 9,248,078 B2 | 2/2016 | Schweiger | |
| 9,321,674 B2 | 4/2016 | Ritzberger | |
| 2003/0099062 A1 * | 5/2003 | Kataoka | C03C 10/0027 360/99.12 |
| 2004/0221615 A1 * | 11/2004 | Postupack | C03C 21/002 65/30.14 |
| 2007/0031515 A1 * | 2/2007 | Stucky | A61K 33/24 424/724 |
| 2007/0042889 A1 | 2/2007 | Apel | |
| 2009/0100873 A1 * | 4/2009 | Allan | C03B 17/064 65/85 |
| 2012/0052302 A1 * | 3/2012 | Matusick | C03C 15/00 428/410 |
| 2012/0135195 A1 * | 5/2012 | Glaesemann | B23K 26/073 428/156 |
| 2012/0236526 A1 * | 9/2012 | Weber | C03C 21/002 361/807 |
| 2013/0295523 A1 | 11/2013 | Durschang | |
| 2014/0225290 A1 | 8/2014 | Ritzberger | |
| 2014/0252272 A1 | 9/2014 | Durschang | |
| 2014/0366579 A1 * | 12/2014 | Antoine | C03C 21/001 65/30.14 |
| 2015/0044445 A1 * | 2/2015 | Garner | C03C 23/0025 428/220 |
| 2016/0039588 A1 * | 2/2016 | Sheehan | B65D 71/70 269/40 |

OTHER PUBLICATIONS

R.R. Seghi et. al.; Effects of Ion Exchange on Hardness and Fracture Toughness of Dental Ceramics; the International Journal of Prosthodontics; vol. 5 No. 4, 1992; pp. 309-314.

International Search Report; PCT/EP2016061414; Jul. 29, 2016 (completed); dated Aug. 2016.

International Preliminary Report on Patentability; PCT/EP2016061414; Jul. 29, 2016 (completed); dated Aug. 8, 2016.

Written Opinion of the International Searching Authority; PCT/EP2016061414; Jul. 29, 2016 (completed); dated Aug. 8, 2016.

* cited by examiner

METHOD TO INCREASE THE STRENGTH OF A FORM BODY OF A LITHIUM SILICATE GLASS CERAMIC

THE CROSS-REFERENCE TO RELATED APPLICATIONS

This patent application claims the benefit of and priority to German Patent Application No. 10 2015 108 169.5, filed on May 22, 2015, which is herein incorporated by reference for all purposes.

TECHNICAL FIELD

The invention relates to a method to increase the strength of a form body comprising a lithium silicate glass ceramic in the form of a dental object, in particular a bridge, or a part of a dental object, wherein the form body, once it has a desired final geometry and following application of a material that influences the surface of the form body, such as a smoothing and/or color-imparting material, such as a glaze material, veneering material and/or stain material, is subject to a heat treatment.

BACKGROUND OF THE INVENTION

A proven method in dental technology has been to use a lithium silicate glass ceramic as a blank for the fabrication of dental restorations because of its strength and biocompatibility. It has been found to be an advantage if, for a lithium silicate blank that contains lithium metasilicate as the main crystal phase, machine working is possible without difficulty, without high tool wear. Upon subsequent heat treatment, in which the product is converted into a lithium disilicate glass ceramic, it then has a high strength. It also has good optical properties and a sufficient chemical stability. Corresponding methods are disclosed in, for example, DE 197 50 794 A1 or DE 103 36 913 B4.

To achieve a high strength and at the same time a good translucency, at least one stabilizer from the group zirconium oxide, hafnium oxide or a mixture thereof, in particular zirconium oxide, is added to the raw materials in the form of lithium carbonate, quartz, aluminum oxide etc., i.e., the usual starting components. Attention is drawn here, for example, to DE 10 2009 060 274 A1, WO 2012/175450 A1, WO 2012/175615 A1, WO 2013/053865 A2 or EP 2 662 342 A1.

The publications of I. L. Denry et. al., Enhanced Chemical Strengthening of Feldspathic Dental Porcelain, J Dent Res, October 1993, pages 1429 to 1433, and R. R. Seghi et. al., Effects of Ion Exchange on Hardness and Fracture Toughness of Dental Ceramics, The International Journal of Prosthodontics, Volume 5, No. 4, 1992, pages 309 to 314, disclose studies of composite ceramics which are comprised of feldspathic glass types in which leucite precipitates may be present. To increase strength, it was proposed to replace sodium ions by lithium ions and then to replace lithium ions by potassium ions in a two-step process. Smaller ions can also be replaced by rubidium ions. This enabled an increase in strength of up to a maximum of 80% if rubidium oxide was used. Rubidium, however, has the disadvantage that the heat expansion coefficient of the ceramics is increased.

DE 30 15 529 A1 discloses a method to improve the mechanical strength of dental porcelain. In this method a restoration is coated with enamel so that there is an exchange of alkali ions in the enamel. For this purpose the restoration is immersed in a bath of melted salt at a temperature between 200° C. and the transition point of the enamel.

U.S. Pat. No. 4,784,606 A discloses a dental brace of glass, the strength of which is increased by ion exchange.

A method for increasing the hardness of a silicate glass object, such as a bottle is disclosed in DE 24 01 275 A1 the object is preferably heated to at least 370° C. and is sprayed with a pulverized mixture of alkali metal salts. This enables ion exchange which increases strength.

SUMMARY OF THE INVENTION

In one aspect, the present invention is directed to a method to increase the strength of a form body of lithium silicate glass ceramic in the form of a dental object comprising the steps of: applying a material to the surface of the form body except for at least one region of the form body; applying a melt or a paste of a salt or a melt or a paste including a salt of an alkali metal or a number of alkali metals with ions of greater diameter than lithium ions to the at least one region of the form body; after the step of applying the melt of paste, heat treating the form body to generate a surface compressive stress through the replacement of lithium ions by alkali ions of greater diameter in the at least one region covered by the melt of paste, wherein the at least one region of the form body is in contact with the melt or paste for a time t at a temperature T; and removing the melt or paste from the form body.

In another aspect, the present invention is directed to a form body of lithium silicate glass ceramic comprising a surface of the form body; a coating that is confined exclusively to one or more regions of the surface of the form body; and at least one region of the surface of the form body not covered by the coating of the surface of the form body; wherein a compressive stress is generated through the replacement of lithium ions by alkali metal ions of greater diameter than the lithium ions.

In yet another aspect, it is contemplated that the present invention has one or any combination of the following features: wherein the form body during the ion exchange is completely covered by the melt or the paste; wherein a portioned quantity of salt is used for the melt; wherein the paste is only applied to the at least one region of the form body not covered by the material; wherein the at least one region of the form body that is subject to a tensile stress remains uncovered by the material; wherein the at least one region includes at least a plurality of regions of the form body which are subject to a tensile stress, which does not have a coating that is formed by application of the material and subsequent heat treatment; further comprising the step of preparing a salt body from the salt as the portioned quantity from the alkali metal/alkali metals through pressing or compression and that the salt body is laid on the form body or the form body is laid directly or indirectly on the salt body and then the salt body is melted; further comprising the step of laying the form body in a receptacle having perforations, and that thereafter (i) the receptacle with the form body is dipped in the melt, or (ii) the receptacle with the form body is introduced into the salt and the salt is then melted, or (iii) the receptacle with the form body is placed on the salt or the salt body and the salt is melted concurrently with immersion of the form body in the melt which is forming; further comprising the step of enveloping the form body with a heat-resistant foil that contains the portioned quantity of salt and that the salt is then melted; wherein the portioned salt is made available in a receptacle with a closure that can be removed; wherein the alkali metal salt, which enables ion exchange, is a phosphate salt, and is added for the binding of lithium ions; wherein the alkali metal ions are selected from the group consisting of Na, K, Cs, Rb ions, or any combination thereof to generate the surface compressive stress; further comprising the step of annealing the form body in a melt including potassium ions, or a melt containing sodium ions, or in a melt containing a mixture of potassium ions and sodium ions; further comprising the step of annealing the form body at a temperature T where T≥300° C., for a time t; further comprising the step of preparing the form body from a glass melt which includes at least the following as starting components: $SiO_2$, $Al_2O_3$, $Li_2O$, $K_2O$, at least one nucleating agent, and at least one stabilizer; wherein the form body or a blank from which the form body is manufactured, is prepared from a glass melt that includes the following components in percentage by weight:

$SiO_2$ 50-80,
at least one nucleating agent 0.5-11
$Al_2O_3$ 0-10,
$Li_2O$ 10-25,
$K_2O$ 0-13,
$Na_2O$ 0-1,
$ZrO_2$ 0-20,
$CeO_2$ 0-10,
$Tb_4O_7$ 0-8,
optionally an oxide or a number of oxides of an earth alkali metal or a number of earth alkali metals selected from the group consisting of magnesium, calcium, strontium, and barium 0-20,
optionally one or more additives selected from the group $B_2O_3$, $MnO_2$, $Fe_2O_3$, $V_2O_5$, $TiO_2$, $Sb_2O_3$, ZnO, $SnO_2$ and fluorides 0-6,
optionally one or more oxides of the rare earth metals with the atomic numbers 57, 59-64, and/or 66-71, 0-5; wherein the glass melt includes the following as starting components in percentage by weight
$SiO_2$ 58.1±2.0
$P_2O_5$ 5.0±1.5
$Al_2O_3$ 4.0±2.5
$Li_2O$ 16.5±4.0
$K_2O$ 2.0±0.2
$ZrO_2$ 10.0±0.5
$CeO_2$ 0-3,
$Tb_4O_7$ 0-3,
$Na_2O$ 0-0.5.
wherein the blank is formed from the glass melt in the course of cooling or following cooling to room temperature, said blank then being subject to at least one first heat treatment W1 at a temperature $T_{W1}$ for a time $t_{W1}$, wherein 620° C.≤$T_{W1}$≤800° C., and/or 1 minute≤$t_{W1}$≤200 minutes; wherein the first heat treatment W1 is carried out in two steps, wherein in particular in the first step a temperature $T_{St1}$ is set where 630° C.≤$T_{St1}$≤690° C. and/or in the second step a temperature $T_{ST2}$ where 720° C.≤$T_{St2}$≤780° C. and/or the heating rate $A_{St1}$ up to the temperature $T_{St1}$ is 1.5 K/minute≤$A_{St1}$≤2.5 K/minute and/or the heating rate $A_{St2}$ up to the temperature $T_{St2}$ is 8 K/minute≤$T_{St2}$≤12 K/minute; wherein the lithium silicate glass ceramic blank is subjected, after the first heat treatment W1, to a second heat treatment W2 at a temperature $T_{W2}$ for a time $t_{W2}$, wherein 800° C.≤$T_{W2}$≤1040° C., and/or 2 minutes≤$t_{W2}$≤200 minutes; wherein after the first or second heat treatment step, the form body is prepared from the blank through grinding and/or milling or pressing, wherein the heat treatment step or steps is/are carried out during or after pressing; wherein the form body or at least one region not covered by the coating, is coated with a viscous solution or dispersion of the salt as the paste; wherein the paste is applied to the form body or to the at least one region not covered by the material through spraying on to the form body; further comprising the step of preparing the paste by mixing the salt with at least one substance selected from the group consisting of a non-flammable substance, monohydric or polyhydric alcohols, halogenated hydrocarbon compound, water, and a mixture of one or more substances; wherein the paste is applied to all the surfaces of the form body at a thickness D of at least 0.5 mm; wherein there is no coating at least in a basal region of the form body; wherein there is no coating in the region of the at least one region subject to a tensile stress of the form body; wherein the alkali metal ions are selected from the group consisting of Na, K, Cs, Rb ions and any combination thereof; wherein a glass phase of the form body or a blank from which the form body is prepared, includes at least one stabilizer that is in the form of $ZrO_2$, that increases the strength of the form body, the concentration of which in the starting composition of the form body is 8-12% by weight; wherein the form body is prepared from a glass melt that contains the following components in percentage by weight $SiO_2$ 52-70,
$P_2O_5$ 0.5-11,
$Al_2O_3$ 0.5-5,
$Li_2O$ 13-22,
$K_2O$ 0.5-8,
$Na_2O$ 0-0.5,
$ZrO_2$ 4-16,
$CeO_2$ 0-10,
$Tb_4O_7$ 0-8,
optionally an oxide or a number of oxides of an earth alkali metal or a number of earth alkali metals selected from the group consisting of magnesium, calcium, strontium, barium, and any combination thereof 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$, fluorides, and any combination thereof 0-6,
optionally one or more oxides of the rare earth metals with the atomic numbers 57, 59-64, 66-71, 0-5; wherein the form body is prepared from a glass melt contains has the following components in percentage by weight:
$SiO_2$ 58.1±2.0
$P_2O_5$ 5.0±1.5
$Al_2O_3$ 4.0±2.5
$Li_2O$ 16.5±4.0
$K_2O$ 2.0±0.2
$ZrO_2$ 10.0±0.5
$CeO_2$ 0-3,
$Tb_4O_7$ 0-3,
$Na_2O$ 0-0.5,
with a total sum of 100% by weight; wherein the form body has a glass phase in the range 20-65% by volume; wherein the form body includes lithium silicate crystals between 35% and 80% by volume of the form body; wherein the percentage of alkali ions replacing the lithium ions, commencing from the surface of the region not covered by coating down to a depth of 10 μm is in the range 5-20% by weight, and/or at a depth between 8 and 12 μm from the surface the percentage of alkali ions is in the range 5-10% by weight, and/or at a layer depth of between 12 and 14 μm from the surface the percentage of alkali ions is in the range 4-8% by weight, and/or at a depth from the surface between 14 and 18 μm the percentage of alkali ions is in the range 1-3% by weight; or any combination thereof.

BRIEF DESCRIPTION OF THE DRAWINGS

Further details, advantages and characteristics of the invention derive not just from the claims, the characteristics to be derived from them—alone and/or in combination—but also from the examples given below.

FIG. 1 A schematic representation of a bridge as a form body, and FIG. 2 A schematic representation of the test apparatus set-up for three-point flexural strength measurement.

DETAILED DESCRIPTION OF THE INVENTION

Figure 1:
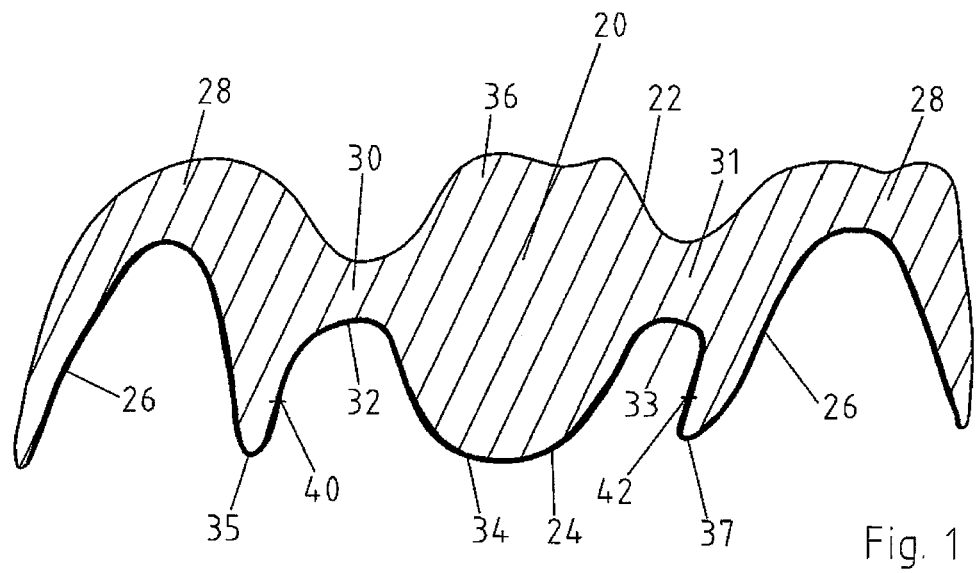

The aim of the present invention is to develop a method of the aforementioned type further so that using simple process technology measures the strength of the body is increased, in particular in regions that are subject to a tensile stress.
In a further aspect, there should be the possibility of preventing impurities in the form body through the measures necessary to increase strength.

The aim of the invention is substantially achieved in that the material, such as glaze material, veneering material and/or stain material, is applied to the surface apart from at least one region, and thereafter the heat treatment is carried out to yield a fired coating and then to create a surface compressive stress through replacement of lithium ions by alkali ions of greater diameter, at least the region not covered by the coating is covered with a melt or paste consisting of or containing a salt of an alkali metal or a number of alkali metals with ions of greater diameter, such that the body is in contact with the melt or paste over a time t at a temperature T and that the melt or paste is then removed from the body.

By applying the inventive method after the form body, like a bridge, has been manufactured and a coating has been applied and fired, the strength of the dental form body is increased especially in those regions where high tensile stress occur, i.e., in particular in the basal region. For a bridge this is, for example, the basal region of a connector. To this end the coating material is not applied in those regions in which corresponding tensile stresses occur. The absence of the coating in this region does not adversely affect the aesthetics of the dental form body since the tensile stresses are fundamentally seen in regions that extend basally so that the occlusal, labial and buccal regions can be provided in the usual manner with a fired coating, such as a glaze, veneering or stain material.

According to the invention in those regions in which particularly high tensile stresses are encountered the coating material that in particular influences the aesthetics of the dental form body is not applied, so that upon subsequent firing, i.e., heat treatment, there is no layer of the coating material, such as glaze, veneering ceramic or stain. In those regions that are not covered by the coating ion exchange can take place, i.e., the lithium ions are replaced by alkali metal ions of greater diameter, so that the desired surface compressive stress and associated increase in strength will result.

Even if in principle it is sufficient for the material that enables ion exchange—be it the melt or the paste—to be applied exclusively to the region that does not have the coating resulting from firing, it is nevertheless preferred for the form body to be fully covered by the melt or paste during the ion exchange process.

To allow untrained persons to carry out the corresponding actions to increase strength, without the danger of impurities contaminating the form body, it is in particular provided that a portioned quantity of salt is to be used for the melt, which can be matched for the external dimensions of the form body which is to be increased in strength. In a further development of the invention the alkali metal or alkali metals salt body is derived through pressing/compression, and the salt body is laid on the form body or the form body is laid directly or indirectly on the salt body and then the salt body is melted.

It is possible to place the form body in a first receptacle such as a basket having perforations so that
  the first receptacle containing the form body is introduced into the melt or
  the salt is introduced into the first receptacle containing the form body and is melted or
  the first receptacle with the form body is placed on the salt which is then melted.

The form body can be laid on the salt containing one alkali metal or a number of alkali metals, or be surrounded by it, so that the salt is then melted, so that the form body is then covered by the melt in the region in which ion exchange is to take place.

As an proposed solution the portioned salt is made available in a receptacle—referred to below as the second receptacle—such as a capsule, with a closure that is removable by tearing off or unscrewing. There is in particular the possibility that the form body is laid on the salt prior to the melting of the salt, or that the salt is melted in the second receptacle and the form body is then immersed in the melt. The invention also embraces the possibility that the form body with a receptacle having perforations—referred to below as the third receptacle—is immersed in the melt present in the second receptacle.

According to a further preferred proposal, the invention teaches that the body is enveloped by a heat-resistant foil as a receptacle—referred to below as the fourth receptacle—in which the portioned quantity of salt is present, and that the salt is then melted.

It was surprisingly found that when the lithium ions present in the form body of lithium silicate glass ceramic are replaced by larger alkali metal ions, a pre-stress and thus a surface compressive stress are generated, leading to a substantial increase in strength.

At the same time it was surprisingly found that the resistance to corrosion was increased. It was found that in addition to an increase in strength through ion exchange, wherein flexural strength values of above 500 MPa, preferably greater than 800 MPa, determined by the three-point bending measurement method specified in DIN EN ISO 6872-2009-01 were obtained, there was also an improvement in chemical resistance which—also determined by the method given in DIN EN ISO 6872-2009-1—yielded a chemical solubility of <95 $\mu g \times cm^{-2}$.

The alkali metal ions used to generate the surface compressive stress are preferably Na, K, Cs and/or Rb ions.

According to the invention the form body which consequently has the geometry of the dental object to be made available, in particular a bridge, crown, cap, inlay, onlay, veneer and preferably a bridge, is annealed in a melt over a period of time t or is enveloped by a paste, which like the melt contains potassium metal ions in a desired concentration, for a period of time t, to enable the desired replacement of lithium ions by alkali metal ions of greater diameter with the consequence that the desired surface compressive stress is created and an increase in strength results.

It is in particular provided for the melt to be portioned in such a way that only the required quantity is made available in the main, so that the form body can be fully immersed in the melt, so that after annealing, i.e., after ion exchange, it is then disposed of, so that for each strength increasing process fresh salt and thus new melt is used, as a result of which compared to methods in which a melt is used more than once there is no contamination. However, there is no departure from the invention if a corresponding melt is used more than once, even though this is not preferred.

It is in particular provided for the form body to be annealed in a melt containing potassium ions, wherein the preferred salt melt is a $KNO_3$, KCl or $K_2CO_3$ salt melt.

Corresponding salts can also be used for the paste.

The invention is preferably characterized in that the form body is annealed in a melt containing potassium ions, in particular a melt containing $KNO_3$, KCl or $K_2CO_3$, or a melt containing sodium ions, in particular a melt containing $NaNO_3$, sodium acetate or sodium salts of organic acids, or in a melt containing a mixture of potassium ions and sodium ions, in particular in a ratio of 50:50 mol. %, preferably in a melt containing $NaNO_3$ and $KNO_3$.

Independently thereof, the form body may be covered with a viscous solution or dispersion of the salt as the paste.

To ensure that there is a constant ion exchange potential during ion exchange, this invention further proposes that lithium ions entering the salt are bound. In particular it is proposed to bind lithium ions by adding a salt such as an alkali metal phosphate salt, like $K_2HPO_4$, to the alkali metal salt enabling ion exchange. The salt containing lithium, such as phosphate, is precipitated in the melt.

Independently thereof, the required ion exchange in the surface region is found to be especially good if the form body is annealed in the melt, or is in contact with a corresponding paste, at a temperature T≥300° C., in particular 350° C.≤T≤600° C., preferred 430° C.≤T≤530° C., for a period of time t≥5 minutes, in particular 0.5 hours≤t≤10 hours, especially preferred 3 hours≤t≤8 hours.

Shorter annealing/contact times in the region of up to 30 minutes are in principle sufficient to create the desired surface compressive stress in the surface region. Insofar as an increase in strength of the form body down to a depth of 20 μm or more is desired, then longer contact/annealing times of, for example, 6 or 10 hours will be necessary, depending on the annealing temperature.

The paste covering the form body, to enable ion exchange, preferably has the same composition in terms of potassium metal ions as the melt referred to above.

To enable the salt to be melted in an energy-conserving and controlled manner to the required temperature and to anneal the form body for the desired length of time the invention is characterized by a heating device with a receptacle—referred to below as the fifth receptacle—which is matched geometrically to the external dimensions of the second receptacle at least over some of its regions. It is possible for the fifth receptacle to be housed in a heating plate of the heating device.

It is preferred for the form body or a blank, from which the form body is obtained derived, to be fabricated from a glass melt, which contains as the starting components at least: $SiO_2$, $Al_2O_3$, $Li_2O$, $K_2O$, at least one nucleating agent, such as $P_2O_5$, and at least one stabilizer such as $ZrO_2$.

The invention is characterized in a particular manner in that not only are lithium ions replaced by larger alkali ions, in particular through potassium and/or sodium ions, but also that to increase strength in the starting substance and thus in the glass phase of the form body/blank from which the form body is derived, at least one dissolved stabilizer, in particular in the form of $ZrO_2$, is contained, wherein the concentration is preferably in the range of 8 to 12% by weight with reference to the initial composition.

In particular the invention is characterized in that the form body/blank is fabricated from a glass melt that has the following composition in percentage by weight:

$SiO_2$ 50-80, preferably 52-70, especially preferred 56-61
nucleating agent, such as $P_2O_5$, 0.5-11, preferably 3-8, especially preferred 4-7
$Al_2O_3$ 0-10, preferably 0.5-5, especially preferred 1.5-3.2
$Li_2O$ 10-25, preferably 13-22, especially preferred 14-21
$K_2O$ 0-13, preferably 0.5-8, especially preferred 1.0-2.5
$Na_2O$ 0-1, preferably 0-0.5, especially preferred 0.2-0.5
$ZrO_2$ 0-20, preferably 4-16, in particular 6-14, especially preferred 8-12
$CeO_2$ 0-10, preferably 0.5-8, especially preferred 1.0-2.5
$Tb_4O_7$ 0-8, preferably 0.5-6, especially preferred 1.0 to 2.0
optionally an oxide or a number of oxides of an earth alkali metal or a number of earth alkali metals from the group magnesium, calcium, strontium and barium 0-20, preferably 0-10, especially preferred 0-5,
optionally one or more additives from the group $B_2O_3$, $MnO_2$, $Fe_2O_3$, $V_2O_5$, $TiO_2$, $Sb_2O_3$, ZnO, $SnO_2$ and fluorides 0-6, preferably 0-4
optionally one or more oxides of the rare earth metals with the atomic numbers 57, 59-64, 66-71, in particular lanthanum, yttrium, praseodymium, erbium, and europium, 0-5, preferably 0-3
wherein the total sum is 100% by weight.

"Optionally an oxide or a number of oxides" means that it is not absolutely necessary for one or more oxides to be contained in the glass melt.

In particular the body/blank has the following composition in percentage by weight:

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 0-3, preferably 1.5 ± 0.6 |
| $Tb_4O_7$ | 0-3, preferably 1.2 ± 0.4, |
| $Na_2O$ | 0-0.5, preferably 0.2-0.5 | wherein the total sum is 100% by weight.

In embodiment the invention is characterized in that the blank is formed from the glass melt during cooling or after cooling to room temperature, with the blank then undergoing at least a first heat treatment W1 at a temperature $T_{W1}$ over a period of time $t_{W1}$, wherein 620° C.≤$T_{W1}$≤800° C., in particular 650° C.≤$T_{W1}$≤750° C., and/or 1 minute≤$t_{W1}$≤200 minutes, preferably 10 minutes≤$t_{W1}$≤60 minutes. The form body is fabricated from the blank/heat-treated blank.

Nuclei and lithium metasilicate crystals are formed during the first heat treatment step. A corresponding lithium silicate glass ceramic blank can be formed through working into a form body, i.e., the dental object, without difficulty, wherein the tool wear is minimal.

The form body can also be fabricated through pressing from a blank or pellets of the above-described composition, wherein the one or more heat treatment steps can be carried out during the pressing procedure or after it.

In particular to obtain the final crystallization, in particular to produce lithium disilicate crystals or transform the metasilicate crystals into disilicate crystals it is provided for the lithium silicate glass ceramic blank after the first heat treatment W1 to undergo a second heat treatment W2 at a temperature $T_{W2}$ over a time $t_{W2}$, wherein 800° C.≤$T_{W2}$≤1040° C., preferably 800° C.≤$T_{W2}$≤900° C. and/or 2 minutes≤$t_{W2}$≤200 minutes, preferably 3 minutes≤$t_{W2}$≤30 minutes.

The following temperature values and heating rates are preferably chosen for the heat treatment steps leading to a pre-crystallization/final crystallization. With regard to the first heat treatment W1 it is in particular provided for a two-step approach, wherein a first holding stage is in the range 640° C. to 680° C. and a second holding stage is in the range 720° C. to 780° C. In each stage the heated blank is held at a temperature for a period of time; in the first stage this is preferably between 35 and 45 minutes and in the second stage preferably between 15 and 25 minutes.

The blank is worked through grinding or milling either after the first heat treatment stage or after the second heat treatment stage, but preferably after the second heat treatment stage, to obtain the form body of the desired geometry.

According to the state of the art the dental object, i.e., the form body, may also be fabricated by pressing.

The form body having in principle the end geometry of the dental object is in particular polished by hand so that the coating material, such as stain material, veneering material and/or glaze material, is applied to the desired region and firing carried out. This procedure may be carried out once or a number of times, and is performed in the temperature range 650° C. to 800° C. The material is applied in the process so that the fired coating layer is developed primarily only in the labial, buccal and occlusal regions so that the desired aesthetic effect attainable through the coating remains visible. In particular there is no material application in the basal region in which after use of the dental object in a jaw region tensile stresses are seen. The corresponding material, such as glaze material, veneering material and/or stain material,—as with the state of the art—is not applied to the inner region of the form body, which for example is laid on a residual tooth or a bridge abutment. With a bridge this is the inner surface, i.e., the inner surface of a bridge anchor which encompasses a bridge abutment.

The form body with fired coating layer over regions is then annealed in a melt or the form body is covered with a paste that contains the required alkali metal ions.

To this end the form body, which is at room temperature, is placed in contact with the salt or covered with the paste at room temperature, and the salt/paste is melted. In particular it is provided for the form body in the melt to be annealed/contacted with a corresponding paste at a temperature $T \geq 300°$ C., in particular $350°$ C.$\leq T \leq 600°$ C., preferred $430°$ C.$\leq T \leq 530°$ C., for a period of time t where $t \leq 5$ minutes, in particular 0.5 hours$\leq t \leq 10$ hours, especially preferred 3 hours$\leq t \leq 8$ hours.

Following removal from the salt melt, cooling and the removal of any adhering residues of salt melt/paste and if necessary to a certain degree working of the form body so made available it may be deployed to the desired degree, in particular as a dental restoration. In view of the increase in strength in the basal region the form body may in particular be a multi-element bridge.

Samples of corresponding form bodies have demonstrated that flexural strength values in excess of 800 MPa can be attained. The values were determined using the three-point method for flexural strength specified in DIN EN ISO 6872:2009-1.

The value for chemical solubility obtained in the hydrolysis test specified in DIN EN ISO 6872:2009-1 was <95 $\mu g \times cm^{-2}$. The method according to the invention therefore not only increased the strength of the form body but also its resistance to corrosion.

In particular it is provided for the salt comprising one or more alkali metal salts to be pressed/compressed into a salt body and for it to be laid on the form body or for the form body to be laid on it and the salt body then melted, so that the salt melt completely envelops the form body and the desired ion exchange can take place. The form body may be accommodated in this process in a receptacle with perforations.

To enable ion exchange to be carried out using a melted salt that as mentioned may be a single alkali salt or a number of alkali salts, or which may contain them, the salt may be made available in aliquots in a receptacle—referred to below as the second receptacle—such as a capsule with a closure that can be removed by tearing or twisting. The second receptacle may at the same time be used as a receptacle for the form body, so that the salt is melted with the form body lying on the salt. There is naturally also the possibility of first melting the salt and then immersing the form body in the melt. The description above also embraces the possibility of first surrounding the form body with salt and then melting it. There is also the possibility of immersing the form body in the melt in a receptacle with perforations such as a wire basket.

To enable a simple handling of the form body, i.e., to facilitate its immersion in the melt or removal from the melt without difficulty in a further development of the invention the form body is introduced with the first receptacle into a receptacle containing the salt, referred to below as the third receptacle.

The invention is also characterized in that the form body is coated with a viscous alkali metal salt solution or dispersion as the paste. To this end it is in particular provided for one or a number of alkali metal salts to be mixed with at least one substance from the following group: a non-flammable substance, monohydric or polyhydric alcohols, a halogenated hydrocarbon compound, water, in particular one of the group 1,4-butanediol, hexanetriol, acetone, water, or a mixture of one or more substances.

For the paste alkali ions, in particular Na or K ions, are used to generate the surface compressive stress.

Independently thereof, the paste may be applied to the form body to the extent that all surfaces are covered, wherein a thickness D of not less than 0.5 mm, preferably 1 mm<D<3 mm, should be maintained. Naturally the paste may also be applied only to those regions in which there is no coating and ion exchange is to take place.

According to the invention it is in particular also provided for the glass phase to be 20-65% by volume, in particular 40-60% by volume.

The invention is consequently characterized by a form body in which the lithium silicate crystals are present in the range 35-80% by volume and in particular 40-60% by volume. Lithium silicate crystals here mean the sum of lithium disilicate crystals, lithium metasilicate crystals and lithium phosphate crystals if $P_2O_5$ is contained.

The form body is in particular characterized in that the concentration of alkali metal ions that replaces the lithium ions, in particular if potassium ions are used, from the surface of the region not covered by the coating down to a depth of 10 μm is in the range 5 to 20% by weight. At a depth between 8 and 12 μm from the surface the alkali ions should be present in the range 5 to 10% by weight. At a depth between 12 and 14 μm from the surface the alkali ions should be present in the range 4 to 8% by weight. At a depth of between 14 and 18 μm from the surface the corresponding range for the alkali ions is between 1 and 3% by weight. The percentage by weight of the alkali ions diminishes from layer to layer.

As mentioned, the percentage by weight values do not take into account the alkali ions already present in the form body. The numerical values hold in particular for potassium ions.

It should firstly be exemplified that as a result of the replacement of lithium ions present in the glass component of a form body of a lithium silicate glass ceramic with alkali metal ions of greater diameter the surface compressive stress is increased, leading to an increase in strength.

In the tests described below at least raw materials, such as lithium carbonate, quartz, aluminum oxide, zirconium oxide, were mixed in a drum mixer until a visually uniform mixture resulted. The compositions according to the data of the manufacturers used for the tests are given below.

The following holds in principle for the tests given below:

The mixture in question was melted at a temperature of 1500° C. for a period of 5 hours in a high-temperature resistant, platinum alloy crucible. The melt was subsequently poured into molds to derive rectangular bodies (blocks). The blocks were subsequently subjected to a two-step heat treatment, designated the first heat treatment step, to create lithium metasilicate crystals as the main crystal phase (1st treatment step). The blocks were thereby heated in the first heat treatment step W1 at a heating rate of 2 K/minute to 660° C. and held at that temperature for 40 minutes. They were then heated further to 750° C. at a heating rate of 10 K/minute. The specimens were held at that temperature for 20 minutes. This heat treatment influences nucleation and lithium metasilicate crystals are formed.

The blocks were then subjected to a second heat treatment step W2 (2nd treatment step) to form lithium disilicate crystals as the main crystal phase. In this heat treatment step the blocks were maintained at a temperature $T_2$ for a period of time $t_2$. The corresponding values are given below. They were then cooled to room temperature.

The cooled blocks were then machined to yield bending rods (specimens) of rectangular shape (3rd treatment step), through grinding of the blocks. The bending rods had the following dimensions: length 15 mm, width 4.1 mm and height 1.2 mm. The specimens were then polished (treatment step 4). A simulated glaze firing was then carried out (5th treatment step), i.e., a temperature treatment without any material being applied to the bending rods (specimens). For some specimens a glaze material was applied after conclusion of the 5th treatment step and a firing carried out (6th treatment step) to create an coating layer. The temperature treatment (firing) was carried out at a temperature between 650° C. and 800° C.

Figure 2:
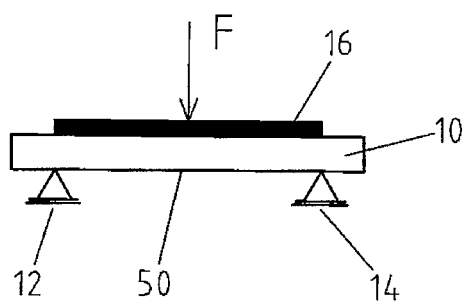

In this procedure, as can be seen schematically in FIG. 2, the glaze may be applied exclusively to that side of the specimens (6th treatment step) on which a loading piston and thus a force F acts so that a three-point measurement of flexural strength is carried out as specified in DIN EN ISO 6872:2009-01. As FIG. 2 further makes clear, no material is applied to the opposite side 50 so that no coating can result upon firing. The glaze or glaze layer is indicated by the number 16 in FIG. 2. The rectangular specimen itself is indicated by the number 10. The Figure also shows that the side surfaces of the specimen 10 and the front faces are not coated.

The three-point flexural strength measurements were carried out as specified in DIN EN ISO 6872:2009-01. For this purpose the specimens (small rods) 10 were mounted on two supports 12, 14 at a distance of 10 mm apart as shown in FIG. 2. A loading piston acted on the specimens between the rods 10, with the tip in contact with the specimen having a radius of 0.8 mm.

For the fabrication of the blocks the following initial composition was adopted (in percentage by weight) according to the data of the manufacturers, to derive lithium silicate glass and therefrom lithium silicate glass ceramic material.

| | |
|---|---|
| $SiO_2$ | 58.1-59.1 |
| $P_2O_5$ | 5.8-5.9 |
| $Al_2O_3$ | 1.9-2.0 |
| $Li_2O$ | 18.5-18.8 |
| $K_2O$ | 1.9-2.0 |
| $ZrO_2$ | 9.5-10.5 |
| $CeO_2$ | 1.0-2.0 |
| $Tb_4O_7$ | 1.0-1.5 |
| $Na_2O$ | 0-0.2 |

The glass phase was in the range 40-60% by volume.

The final crystallization (second heat treatment step) to form the lithium disilicate crystals was carried out at a temperature $T_2$=830° C. for a period of time $t_2$=5 minutes.

A total of 70 rods were prepared and treatment steps 1 to 5 carried out for them. The following tests were performed with them.

Test Series #1

Ten of these rods, for which treatment steps 1-5 were performed, without material application, were then tested to determine their strength. The mean value obtained in the three-point flexural strength test referred to above was 358 MPa.

Test Series #2

Ten further rods were then annealed in a salt bath of technically pure $KNO_3$ at a temperature of 480° C. for 10 hours. The rods were then removed from the melt and the melt residues removed using warm water. Three-point flexural strength measurements were then carried out as described above. The mean three-point flexural strength value was 870 MPa.

Test Series #3

Ten of the 70 rods were annealed in a technically pure $KNO_3$ salt bath at a temperature of 480° C. for 10 hours. A glaze material was then partially applied to the rods—as shown in FIG. 2—to one side upon which the force F acts and the specimens were fired at a temperature $T_3$=660° C., maintained for a period $t_3$=60 seconds. A mean three-point flexural strength value of 407 MPa was obtained.

Test Series #4

Ten rods as in test series #3 were first annealed in a technically pure $KNO_3$ salt bath at a temperature of 480° C. for 10 hours. A glaze material was then partially applied to the rods to the side upon which the force F acts and the specimens were fired at a temperature $T_3$=680° C. maintained for a period $t_3$=60 seconds. A mean three-point flexural strength value of 381 MPa was obtained.

Test Series #5

Ten further rods—as in test series #3 and #4—were first annealed in a technically pure $KNO_3$ salt bath at a temperature of 480° C. for 10 hours. As before, a glaze material was then partially applied to the side upon which the force F acts and the specimens were fired at a temperature $T_3$=750° C., maintained for a period $t_3$=90 seconds. A three-point flexural strength value of 326 MPa was obtained.

Test Series #6

A further 10 rods were partially coated with a glaze material on that side on which the stamp acts in the three-point flexural strength measurement test, i.e., the force F, as indicated in FIG. 2. The region 50 which is subject to tensile stresses therefore remained uncovered. The same held for the sides. Firing was carried out at a temperature $T_3$=750° C.

for a period $t_3$=90 seconds. The specimens were then annealed as described for test series #2 in a technically pure $KNO_3$ salt bath at a temperature of 480° C. for 10 hours. The specimens were removed from the melt and melt residues removed and three-point flexural strength measurements carried out, and as described above the force was applied to that side of the rod which bore the coating layer 16 (glaze). A mean three-point flexural strength value of 874 MPa was obtained.

Test Series #7

The remaining 10 rods were coated in their entirety with a glaze material. A glaze firing was then carried out at a temperature $T_3$=750° C. for a period $t_3$=90 seconds. The specimens were then annealed as described for test series #2 in a technically pure $KNO_3$ salt bath at a temperature of 480° C. for 10 hours. The specimens were removed from the melt and melt residues removed and three-point flexural strength measurements carried out as described above. The three-point flexural strength value was 353 MPa.

It was found in these tests that when ion exchange was carried out to increase the hardness of the surfaces prior to further heat treatment—in this case the glaze firing—the surface compressive stress previously attained through the ion exchange was reduced again. The likely reason for this was that during the further heat treatment the potassium ions diffuse further into the specimens to a degree that the surface compressive stress is lost.

If a coating (glaze) is applied to all parts of the specimen bodies then the glaze forms a diffusion block so that an increase in the hardness of the surfaces is not possible in principle.

A partial application of a material required for a coating by contrast does not influence the desired creation of a surface compressive stress through the replacement of lithium ions by alkali metal ions of greater diameter, insofar as at least the zone subject to tensile stress remains uncovered, i.e., has no coating applied to it.

FIG. 1 shows a dental form body in the form of a three-element bridge 20 that is fabricated from a lithium disilicate ceramic material, with its outer surface 22 provided with a glaze in the labial, buccal and occlusal regions and at the very maximum partially in basal region 24. The basal region 24, and in regions 32, 33 of the connectors 30, 31 and the basal region 34 of the intermediate member 36 are free of glaze. To arrive at this the bridge 20 was only partially covered with a glaze material or other material forming a coating through firing such as a stain material or composite ceramic material.

The basal region 24 not covered by the glaze ends in the embodiment example at a distance to the bridge anchor edge 35, 37. This allows a layer which elicits an aesthetically pleasing effect to be applied between the corresponding bridge anchor edge 35, 37 and in regions of the basal regions 32, 33, 34. This region to which the layer has been applied extends in FIG. 1 between the respective bridge anchor edge 35/37 and the near point 40/42. In the sectional representation the basal regions 32, 33 and the basal region 34 of the tooth bridge 20 extend partially between the points 40, 42 and remain uncovered, i.e., do not have a layer applied to them which elicits an aesthetically pleasing effect to facilitate ion exchange in these regions. The internal surface of the bridge 20, i.e., the inner region of the bridge anchor 28, is also uncovered so that—as with the state of the art—imprecise fit through a glaze can be avoided.

The strength of corresponding bridges 20 of a lithium silicate ceramic material with in particular lithium disilicate crystals as the main crystal phase is significantly higher than those for which the procedure according to the invention was not carried out. It is possible to obtain values that are more than 100% higher than those for bridges fabricated according to the state of the art. The prerequisite is that lithium ions are replaced by alkali metal ions of greater diameter according to the teaching of the invention in regions in which an elevated tensile stress is seen, i.e., in particular in the basal regions, i.e., for bridges in particular at the undersides of intermediate elements 36 and connectors 30, 31 that are regions of the outer surface.

The invention claimed is:

1. A method to increase the strength of a form body of lithium silicate glass ceramic in the form of a dental object comprising the steps of:
   providing the form body, which was prepared from at least the following starting components: $SiO_2$, $Al_2O_3$, $Li_2O$, $K_2O$, at least one nucleating agent, and at least one stabilizer;
   applying a coating material to the surface of the form body except for at least one surface region of the form body, said partially coated form body being subjected to at least one first heat treatment;
   applying a melt or a paste including a salt of an alkali metal and a number of alkali metals with ions of greater diameter than lithium ions to the at least one region of the heat-treated partially coated form body, wherein the melt or the paste includes a composition different from the coating material, wherein an aliquoted quantity of salt is used for the melt or paste, wherein the salt of an alkali metal is an alkali metal phosphate salt and the alkali metals with alkali ions of greater diameter than lithium ions is selected from the group consisting of Na, K, Cs, Rb and combinations thereof ions;
   after the step of applying the melt or paste, annealing the multiple coated form body to generate a surface compressive stress through the replacement of lithium ions by the alkali ions of greater diameter in the at least one region covered by the melt or paste, wherein the at least one region of the form body is in contact with the melt or paste for a temperature where 350° C.≤T≤600° C. and a time t where 0.5 hours ≤t≤10 hours; and
   removing the melt or paste from the heat treated multiple coated form body.

2. The method according to claim 1, wherein the form body during the ion exchange is completely covered by the melt or the paste.

3. The method according to claim 1, wherein a portioned quantity of salt is used for the melt.

4. The method according to claim 3, further comprising the step of enveloping the form body with a heat-resistant foil that contains the portioned quantity of salt and that the salt is then melted.

5. The method according to claim 3, wherein the portioned salt is made available in a receptacle with a closure that can be removed.

6. The method according to claim 1, wherein the paste is only applied to the at least one region of the form body not covered by the material.

7. The method according to claim 1, wherein the at least one region of the form body that is subject to a tensile stress remains uncovered by the material.

8. The method according to claim 1, wherein the at least one region includes at least a plurality of regions of the form body which are subject to a tensile stress, which does not have a coating that is formed by application of the material and subsequent heat treatment.

9. The method according to claim 1, further comprising the step of preparing a salt body from the salt as the portioned quantity from the alkali metal/alkali metals through pressing or compression and that the salt body is laid on the form body or the form body is laid directly or indirectly on the salt body and then the salt body is melted.

10. The method according to claim 1, further comprising the step of laying the form body in a receptacle having perforations, and that thereafter
the receptacle with the form body is dipped in the melt, or
the receptacle with the form body is introduced into the salt and the salt is then melted, or
the receptacle with the form body is placed on the salt or the salt body and the salt is melted concurrently with immersion of the form body in the melt which is forming.

11. The method according to claim 1, wherein the alkali metal salt, which enables ion exchange, is a phosphate salt, and is added for the binding of lithium ions.

12. The method according to claim 1, further comprising the step of annealing the form body in a melt including potassium ions, or a melt containing sodium ions, or in a melt containing a mixture of potassium ions and sodium ions.

13. The method according claim 1, wherein the form body or a blank from which the form body is manufactured, is prepared from a glass melt that includes the following components in percentage by weight:
$SiO_2$ 50-80,
at least one nucleating agent 0.5-11
$Al_2O_3$ 0-10,
$Li_2O$ 10-25,
$K_2O$ 0-13,
$Na_2O$ 0-1,
$ZrO_2$ 0-20,
$CeO_2$ 0-10,
$Tb_4O_7$ 0-8,
optionally an oxide or a number of oxides of an earth alkali metal or a number of earth alkali metals selected from the group consisting of magnesium, calcium, strontium, and barium 0-20,
optionally one or more additives selected from the group $B_2O_3$, $MnO_2$, $Fe_2O_3$, $V_2O_5$, $TiO_2$, $Sb_2O_3$, ZnO, $SnO_2$ and fluorides 0-6,
optionally one or more oxides of the rare earth metals with the atomic numbers 57, 59-64, and/or 66-71, 0-5.

14. The method according to claim 13, wherein the glass melt includes the following as starting components in percentage by weight
$SiO_2$ 58.1±2.0
$P_2O_5$ 5.0±1.5
$Al_2O_3$ 4.0±2.5
$Li_2O$ 16.5±4.0
$K_2O$ 2.0±0.2
$ZrO_2$ 10.0±0.5
$CeO_2$ 0-3,
$Tb_4O_7$ 0-3,
$Na_2O$ 0-0.5.

15. The method according to claim 1, wherein the form body is prepared from a blank being subjected to a first heat treatment W1, which is carried out in two steps, wherein in particular in the first step a temperature $T_{St1}$ is set where 630° C.$\leq T_{St1} \leq$690° C. and/or in the second step a temperature $T_{ST2}$ where 720° C.$\leq T_{St2} \leq$780° C. and/or the heating rate $A_{St1}$ up to the temperature $T_{St1}$ is 1.5 K/minute$\leq A_{St1} \leq$2.5 K/minute and/or the heating rate $A_{St2}$ up to the temperature $T_{St2}$ is 8 K/minute$\leq T_{St2} \leq$12 K/minute.

16. The method according to claim 15, wherein the lithium silicate glass ceramic blank is subjected, after the first heat treatment W1, to a second heat treatment W2 at a temperature $T_{W2}$ for a time $t_{W2}$, wherein 800° C.$\leq T_{W2} \leq$1040° C., and/or 2 minutes$\leq t_{W2} \leq$200 minutes.

17. The method according to claim 16, wherein after the first or second heat treatment step, the form body is prepared from the blank through grinding and/or milling or pressing, wherein the heat treatment step or steps is/are carried out during or after pressing.

18. The method according to claim 1, wherein the form body or at least one region not covered by the coating is coated with a viscous solution or dispersion of the salt as the paste.

19. The method according to claim 18, wherein the paste is applied to the form body or to the at least one region not covered by the material through spraying on to the form body.

20. The method according to claim 18, further comprising the step of preparing the paste by mixing the salt with at least one substance selected from the group consisting of a non-flammable substance, monohydric or polyhydric alcohols, halogenated hydrocarbon compound, water, and a mixture of one or more substances.

21. The method according to claim 18, wherein the paste is applied to all the surfaces of the form body at a thickness D of at least 0.5 mm.

* * * * *